United States Patent
Barlow et al.

(10) Patent No.: US 12,232,845 B2
(45) Date of Patent: Feb. 25, 2025

(54) TACTILE STIMULATION DEVICE

(71) Applicant: NUTECH VENTURES, Lincoln, NE (US)

(72) Inventors: Steven M. Barlow, Lincoln, NE (US); Jacob L. Greenwood, Lincoln, NE (US)

(73) Assignee: NUtech Ventures, Lincoln, NE (US)

( * ) Notice: Subject to any disclaimer, the term of this patent is extended or adjusted under 35 U.S.C. 154(b) by 890 days.

(21) Appl. No.: 17/294,257

(22) PCT Filed: Nov. 14, 2019

(86) PCT No.: PCT/US2019/061460
§ 371 (c)(1),
(2) Date: May 14, 2021

(87) PCT Pub. No.: WO2020/102520
PCT Pub. Date: May 22, 2020

(65) Prior Publication Data
US 2022/0015634 A1    Jan. 20, 2022

Related U.S. Application Data

(60) Provisional application No. 62/767,482, filed on Nov. 14, 2018.

(51) Int. Cl.
*A61B 5/00* (2006.01)
(52) U.S. Cl.
CPC .................................. *A61B 5/0053* (2013.01)

(58) Field of Classification Search
CPC ........... A61B 5/00; A61B 5/055; A61B 5/377; A61B 5/4005; A61B 5/0048–0055;
(Continued)

(56) References Cited

U.S. PATENT DOCUMENTS 10,388,024 B2    8/2019   Lee et al.
2010/0030120 A1  2/2010   Graham et al.
(Continued)

FOREIGN PATENT DOCUMENTS

KR    2014065168 A  *  5/2014
KR    1020140065168 A   5/2014
(Continued)

OTHER PUBLICATIONS

English Translation of KR 20140065168 A, Konkuk University Industry-Academic Cooperation Foundation, 8 pages, printed on Oct. 31, 2024,. (Year: 2014).*

(Continued)

*Primary Examiner* — Devin B Henson
*Assistant Examiner* — Jennifer Grace Baires-Tweed
(74) *Attorney, Agent, or Firm* — Suiter Swantz IP (57) ABSTRACT

The present disclosure is directed to a tactile stimulation device. The tactile stimulation device can include at least one pneumatic switch, an applicator connected to the at least one pneumatic switch, and a controller operatively connected to the at least one pneumatic switch. The controller is configured to control the at least one pneumatic switch to connect the applicator to at least one of high pressure, vacuum pressure, and atmospheric pressure to stimulate a nerve ending of a user.

20 Claims, 7 Drawing Sheets

(58) Field of Classification Search
CPC ........ A61B 5/388; A61B 5/4029–4094; A61B 5/40; A61H 9/005; A61H 9/0071; A61N 2/006; A61M 2205/8206
See application file for complete search history.

(56) References Cited

U.S. PATENT DOCUMENTS

| | | |
|---|---|---|
| 2012/0157895 A1 | 6/2012 | Barlow et al. |
| 2015/0133830 A1* | 5/2015 | Dirks ................... A61H 9/0071 601/84 |
| 2017/0300115 A1* | 10/2017 | Kerr ........................ G06F 3/016 |

FOREIGN PATENT DOCUMENTS

| | | | |
|---|---|---|---|
| KR | 101595742 B1 | 2/2016 | |
| WO | WO-2011096705 A2 * | 8/2011 | ............. A61H 7/008 |

OTHER PUBLICATIONS

English Translation of WO 2011096705 A2, Spa Tech Co., Ltd., 10 pages, printed on Oct. 31, 2024,. (Year: 2011).*

International Searching Authority, International Search Report and Written Opinion for International application No. PCT/US2019/061460, mailed Mar. 9, 2020, pp. 1-8.

* cited by examiner

TACTILE STIMULATION DEVICE

CROSS-REFERENCE TO RELATED APPLICATIONS

This patent application claims priority to and all the benefits of U.S. Provisional Patent Application No. 62/767,482 filed on Nov. 14, 2018, which is herein incorporated by reference in its entirety.

FIELD

The present disclosure relates to a tactile stimulation device.

BACKGROUND

Tactile stimulation devices operate by inducing activation of the nerve endings and receptors proximate to a subject's skin. Tactile stimulation has a number of uses, which include testing and diagnosis as well as therapeutic applications. For example, it is common to correlate tactile stimuli with brain activity to determine whether a neuronal path and/or the brain are functioning properly, such as in stroke victims, and/or to provide therapy using patterns of tactile stimulation. Brain activity may be detected in response to tactile stimuli using, for example, functional magnetic resonance imaging (fMRI), magnetoencephalography scanning (MEG), functional near infrared spectroscopy (fNIRS), or electroencephalography (EEG).

The background description provided here is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

The present disclosure is directed to a tactile stimulation device. The tactile stimulation device can include at least one pneumatic switch, an applicator connected to the at least one pneumatic switch, and a controller operatively connected to the at least one pneumatic switch. The controller is configured to control the at least one pneumatic switch to connect the applicator to at least one of high pressure, vacuum pressure, and atmospheric pressure to stimulate a nerve ending of a user.

In other features, the controller is further configured to control the connection of the at least one pneumatic switch to connect the applicator to at least one of high pressure, vacuum pressure, and atmospheric pressure according to a predetermined stimulation pattern.

In other features, the tactile stimulation device includes an input device connected to the controller.

In other features, the input device is configured to provide data representing the predetermined stimulation pattern to the controller.

In other features, the tactile stimulation device includes an enclosure including a quick-release port configured to connect the applicator to the at least one pneumatic switch, a high pressure reservoir disposed in the enclosure, a low pressure reservoir disposed in the enclosure, and a compressor connected to the high pressure reservoir and the low pressure reservoir.

In other features, the compressor comprises a dual-mode compressor that is configured to supply pressurized air to the high pressure reservoir during a first mode of operation and is configured to generate vacuum pressure to remove air from the low pressure reservoir during a second mode of operation.

In other features, the tactile stimulation device includes power/charging circuitry configured to supply power to the controller and the dual-mode compressor.

In other features, the at least one pneumatic switch comprises a plurality of pneumatic solenoids.

In other features, the plurality of pneumatic solenoids are connected to the high pressure reservoir.

In other features, the plurality of pneumatic solenoids are connected to the low pressure reservoir.

The present disclosure is directed to a tactile stimulation device. The tactile stimulation device can include an enclosure, a high pressure reservoir disposed in the enclosure, a low pressure reservoir disposed in the enclosure, a compressor connected to the high pressure reservoir and the low pressure reservoir, at least one pneumatic switch disposed within the enclosure and connected to the high pressure reservoir and the low pressure reservoir, an applicator connected to the at least one pneumatic switch, and a controller disposed within the enclosure and operatively connected to the at least one pneumatic switch. The controller is configured to control the at least one pneumatic switch to connect the applicator to at least one of high pressure, vacuum pressure, and atmospheric pressure to stimulate a nerve ending of a user.

In other features, the controller is further configured to control the connection of the at least one pneumatic switch according to a predetermined stimulation pattern.

In other features, the tactile stimulation device includes input device connected to the controller.

In other features, the input device is configured to provide data representing the predetermined stimulation pattern to the controller.

In other features, the compressor comprises a dual-mode compressor that is configured to supply pressurized air to the high pressure reservoir during a first mode of operation and is configured to generate vacuum pressure to remove air from the low pressure reservoir during a second mode of operation.

In other features, the tactile stimulation device includes power/charging circuitry disposed within the enclosure and configured to supply power to the controller and the dual-mode compressor.

In other features, the at least one pneumatic switch comprises a plurality of pneumatic solenoids.

In other features, the plurality of pneumatic solenoids are connected to the high pressure reservoir.

In other features, the plurality of pneumatic solenoids are connected to the low pressure reservoir.

The present disclosure to a tactile stimulation device. The tactile stimulation device can include an enclosure, a high pressure reservoir disposed in the enclosure, a low pressure reservoir disposed in the enclosure, and a dual-mode compressor disposed in the enclosure and connected to the high pressure reservoir and the low pressure reservoir. The dual-mode compressor configured to supply pressurized air to the high pressure reservoir during a first mode of operation and is configured to generate vacuum pressure to remove air from the low pressure reservoir during a second mode of operation. The tactile stimulation device can also include at least one pneumatic switch disposed within the enclosure and connected to the high pressure reservoir and the low pressure reservoir, an applicator connected to the at least one pneumatic switch, and a controller disposed within the enclosure and operatively connected to the at least one pneumatic switch. The controller is configured to control the at least one pneumatic switch to connect the applicator to at least one of high pressure, vacuum pressure, and atmospheric pressure to stimulate a nerve ending of a user.

BRIEF DESCRIPTION OF THE DRAWINGS

The present disclosure will become more fully understood from the detailed description and the accompanying drawings.

In the drawings, reference numbers may be reused to identify similar and/or identical elements.

DETAILED DESCRIPTION

The present disclosure is directed to a tactile stimulation device. The tactile stimulation device can deliver cutaneous stimulation to one or more regions of a body. For example, applicators connected to the tactile stimulation device can be affixed over the skin of a user's hand, face, and/or feet and deliver pressurized fluid changes to the skin. For example, the fluid may be a gas, such as ambient air. The pressure changes can stimulate mechanosensory nerve endings, and the user's responsive brain function can be monitored using suitable scanning technologies, such as MRI, MEG, fNIRS, EEG, and/or functional transcranial Doppler (fTCD).

The tactile stimulation device can include a controller that controls tactile stimulation. For example, the controller can control one or more pneumatic switches that connect the applicators to high pressure (that is, greater than atmospheric pressure), vacuum pressure, or atmospheric pressure to stimulate the user's nerve endings. The controller can control the applicator connections according to a predetermined stimulation pattern. The predetermined stimulation pattern can be provided to the controller via an input device or stored in memory connected to the controller.

Figure 1:
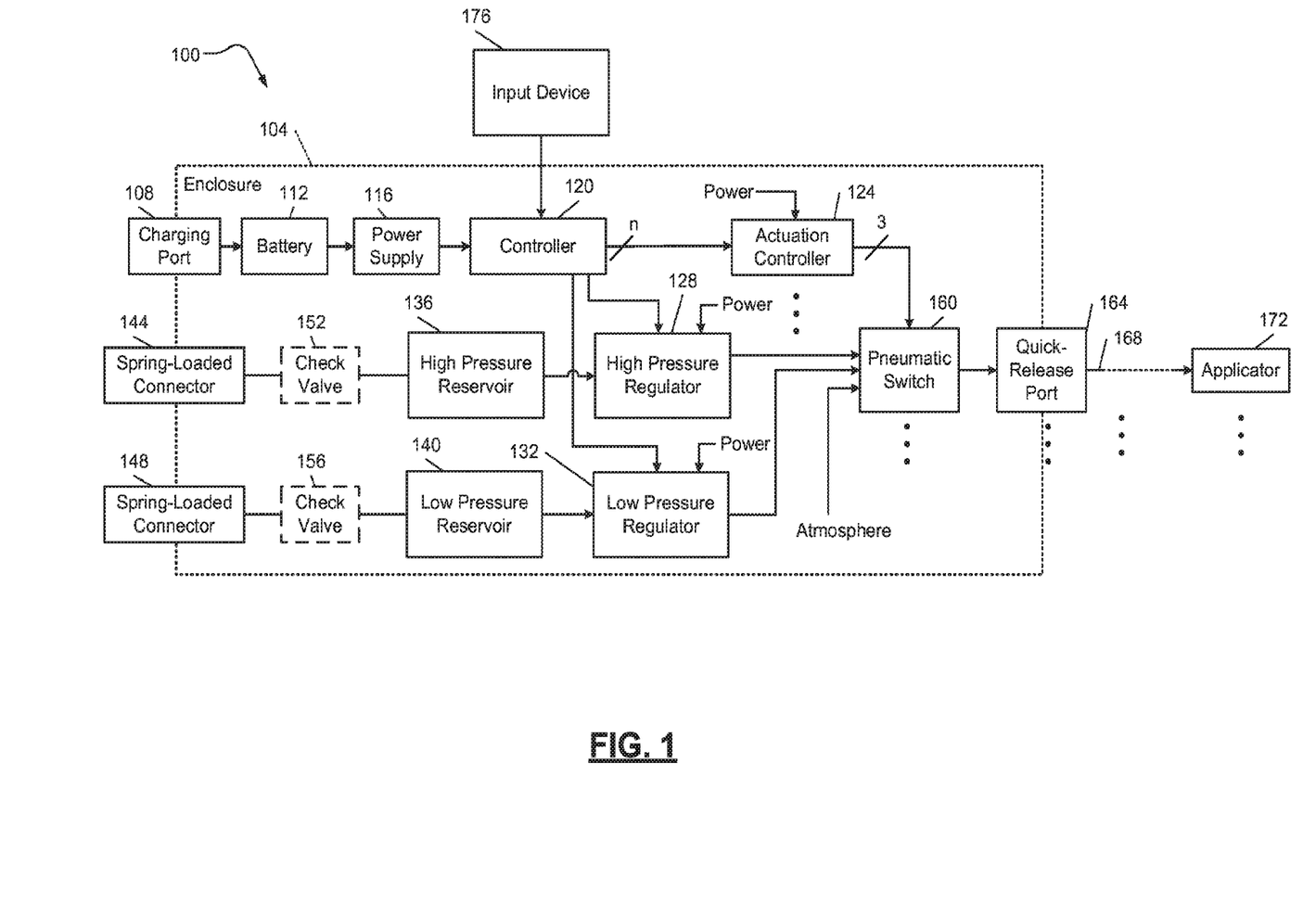
FIG. 1 is a block diagram illustrating a tactile stimulation device in accordance with an example implementation of the present disclosure.

FIG. 1 illustrates an example tactile stimulation device 100. The tactile stimulation device 100 includes an enclosure 104 that encloses components of the tactile stimulation device 100. The enclosure 104 may have sound deadening properties, which may be enhanced with specific sound dampening materials and/or internal baffles. The enclosure 104 provides easy portability of the tactile stimulation device 100 and may contain noise to such an extent that operation of the tactile stimulation device 100 is barely audible or even imperceptible.

A charging port 108, located on the enclosure 104, connects to a battery 112. The charging port 108 can receive a connector that supplies power to the battery 112. In various implementations, the charging port 108 may include a female Universal Serial Bus (USB) connector or a female DC power supply connector (such as a tip and ring connector or a barrel plug connector). A transforming power supply (not shown) may convert AC mains power into a DC voltage for provision to the charging port 108.

The battery 112 supplies power to the power supply 116, and the power supply 116 distributes power to various components within the tactile stimulation device 100. In various implementations, the battery 112 includes a rechargeable lithium-ion battery. The power supply 116 provides power to a controller 120, one or more actuation controllers 124, a high pressure regulator 128, and a low pressure regulator 132. From the power provided by the battery 112, the power supply 116 may generate one or more voltages of power for distribution. For example, the power supply 116 may include one or more voltage regulators and one or more DC-DC conversion circuits, such as a boost circuit, a buck circuit, or a boost/buck circuit.

The tactile stimulation device 100 includes a high pressure (greater than atmospheric) reservoir 136 and a low pressure (less than atmospheric, or, vacuum) reservoir 140. The high pressure reservoir 136 and the low pressure reservoir 140 act as pneumatic capacitors, storing high and low pressures, respectively, for use of the tactile stimulation device 100 without direct access to an air compressor. The high pressure regulator 128 is connected to the high pressure reservoir 136 to generate a specific high pressure. The low pressure regulator 132 is connected to low pressure reservoir to generate a specific low pressure.

A compressor or other source of pressurized air can increase pressure within the high pressure reservoir 136 through a spring-loaded connector 144. For example, an air hose can be connected between a compressed air port on a wall of a hospital and the spring-loaded connector 144, which is opened by the end of the air hose pressing against the spring. To prevent backflow from the high pressure reservoir 136, a check valve 152 can be included between the spring-loaded connector 144 and the high pressure reservoir 136.

The same compressor, operating in suction mode, or a difference source of vacuum, can lower the pressure of the low pressure reservoir 140 via a spring-loaded connector 148. A check valve 156 may be included to prevent the pressure of the low pressure reservoir 140 increasing upon connection to a weak vacuum source (one that has a higher pressure than the current pressure of the low pressure reservoir 140).

The high pressure reservoir 136 and the low pressure reservoir 140 may be pressurized to, as examples only, +3 psi and −3 psi, respectively. This may allow hours of operation before additional high pressure and vacuum sources need to be connected.

The tactile stimulation device 100 also includes a pneumatic switch 160. The pneumatic switch 160 receives the regulated pressures from the high pressure regulator 128 and the low pressure regulator 132. The pneumatic switch 160, as described in more detail below, may include individual solenoids that, in response to a selection signal from the actuation controller 124, open to connect a respective one of the high pressure, low pressure, and atmospheric pressure to a quick-release port 160.

An outlet conduit 168, which may be disposable or reusable, is connected between the quick-release port 164 and an applicator 172. The applicator may be affixed to a patient, such as with adhesive gel or tape. The outlet conduit 168 may be clear plastic tubing. The applicator 172 is a structure that applies pressure or vacuum from the outlet conduit 168 to the patient's skin. For example, the applicator 172 may be a flange that holds an end of the outlet conduit 168 at right angles to the patient's skin.

In various implementations, multiple applicators 172 are attached to different areas of the patient's skin by multiple outlet conduits 168. The tactile stimulation device 100 may therefore include a corresponding number of quick-release ports 164, pneumatic switches 160, and actuation controllers 124. In various implementations, the pneumatic switches 160 may be physically ganged together in groups of five. Similarly, the quick-release ports 164 may be physically ganged together in groups of five.

The enclosure 104 may have a storage compartment for external items, including the outlet conduits 168 and the applicators 172. The storage compartment may be separate from or the same as the main compartment where other items, such as the high pressure reservoir 136 and the low pressure reservoir 140, are located.

The tactile stimulation device 100 can be connected to an input device 176. Users, such as medical personnel, can input desired stimulation data, parameter data related to the user, etc., to the controller 120 via the input device 176. Based on the received data, the controller 120 may specify pressures to the high pressure regulator 128 and to the low pressure regulator 132. In addition, the controller 120 may provide control signals to the actuation controller 124.

The actuation controller 124 may include a simple set of 3 drive circuits (such as three H-bridges) that are directly controlled by the controller 120. In other implementations, the actuation controller 124 may include timing logic that, under the direction of the controller, actuates the drive circuits. For example, the controller 120 may specify a pulse length and an inter-pulse duration (equivalently, a pulse repetition frequency) to the actuation controller 124.

As described in more detail below with respect to FIG. 7, a pulse may include a high-pressure interval and a low-pressure interval with an atmospheric interval in between. The actuation controller 124 may be preprogrammed with lengths of these intervals (which may vary based on the commanded pulse length). In some implementations, these lengths may be commanded by the controller.

The controller 120 may store specific stimulation pattern data and generate control signals based on the stimulation pattern data. For example, a saltatory wave operating at a specific linear speed and repeating at a certain interval may be programmed. Random or pseudorandom variation of the saltatory wave may be part of the stored programming. In various implementations, a clinician may input minimal parameters to the input device 176, and simply initiate preprogrammed sequences. In other implementations, a clinician or researcher may directly specify pulse parameters, such as via a serial interface (for example, USB).

In various implementations, the input device 176 may include an LED or LCD display as well as input buttons. The input device 176 may be mounted to or integrated with the enclosure 104.

Figure 5:
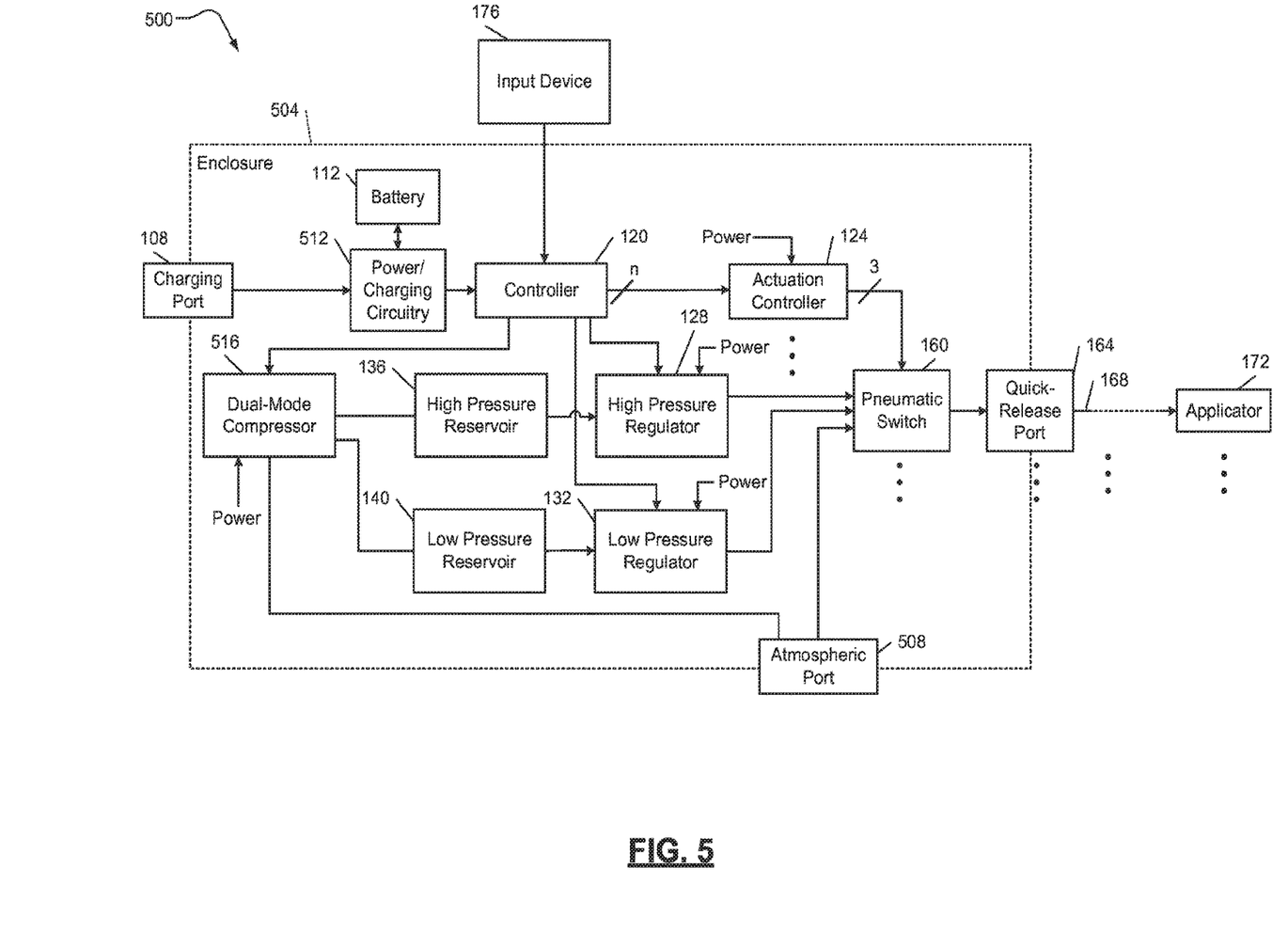
FIG. 5 is a block diagram illustrating a tactile stimulation device in accordance with another example implementation of the present disclosure.

The controller 120 may include a microcontroller (PIC16F18856 from Microchip), and the actuation controllers 124 may include H-Bridge Drivers (DRV8337 from Texas Instruments) and/or pulse-width-modulation (PWM) current controllers for solenoids (DRV110 from Texas Instruments). The tactile stimulation devices 100, 500 may also include a USB-to-UART serial converter (MCP2200 from Microchip) to enable USB connectivity. The spring-loaded connectors 144, 148 may be implemented using Schrader valves. The spring-loaded connectors 144, 148 may include a quick-disconnect panel-mount valve (EW-06360-55 or EW-06361-71 from Cole-Parmer).

Figure 4:
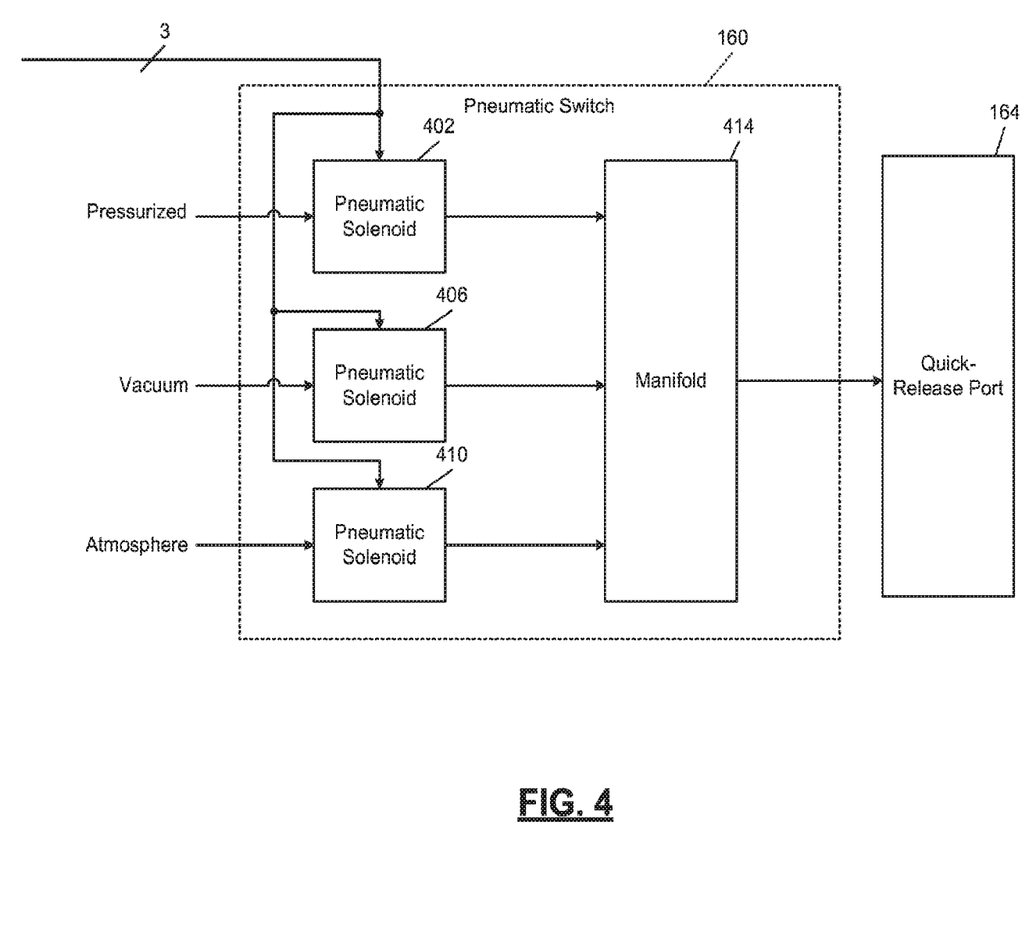
FIG. 4 is a block diagram illustrating a pneumatic switch of the tactile stimulation device in accordance with an example implementation of the present disclosure.

The high pressure regulator 128 may be a positive servo regulator (LFR-512-0505-R4 from Kelly Pneumatics) and the low pressure regulator 132 may be a negative servo regulator (LFR-N512-0505-R4 from Kelly Pneumatics). The pneumatic solenoids 402, 406, 410 may be latching solenoid valves (LHLA0531111H from The Lee Company) or non-latching solenoid valves (LHDB0442145D from The Lee Company) or high flow cartridge style solenoids (from Humphrey Products).

The outlet conduits 168 may include silicone or polyethylene tubing having an inner diameter of 1/16" and an outer diameter of 1/8". The tactile stimulation devices 100, 500 can include a 10-port connector (EW-31052-41 or EW-31052-21 from Cole-Parmer) to provide connections between the applicators 172 and the outlet conduits 168. The pressure reservoirs 136, 140 may be formed from polyvinyl chloride (PVC), such as from schedule 40 PVC pipe.

Figure 2:
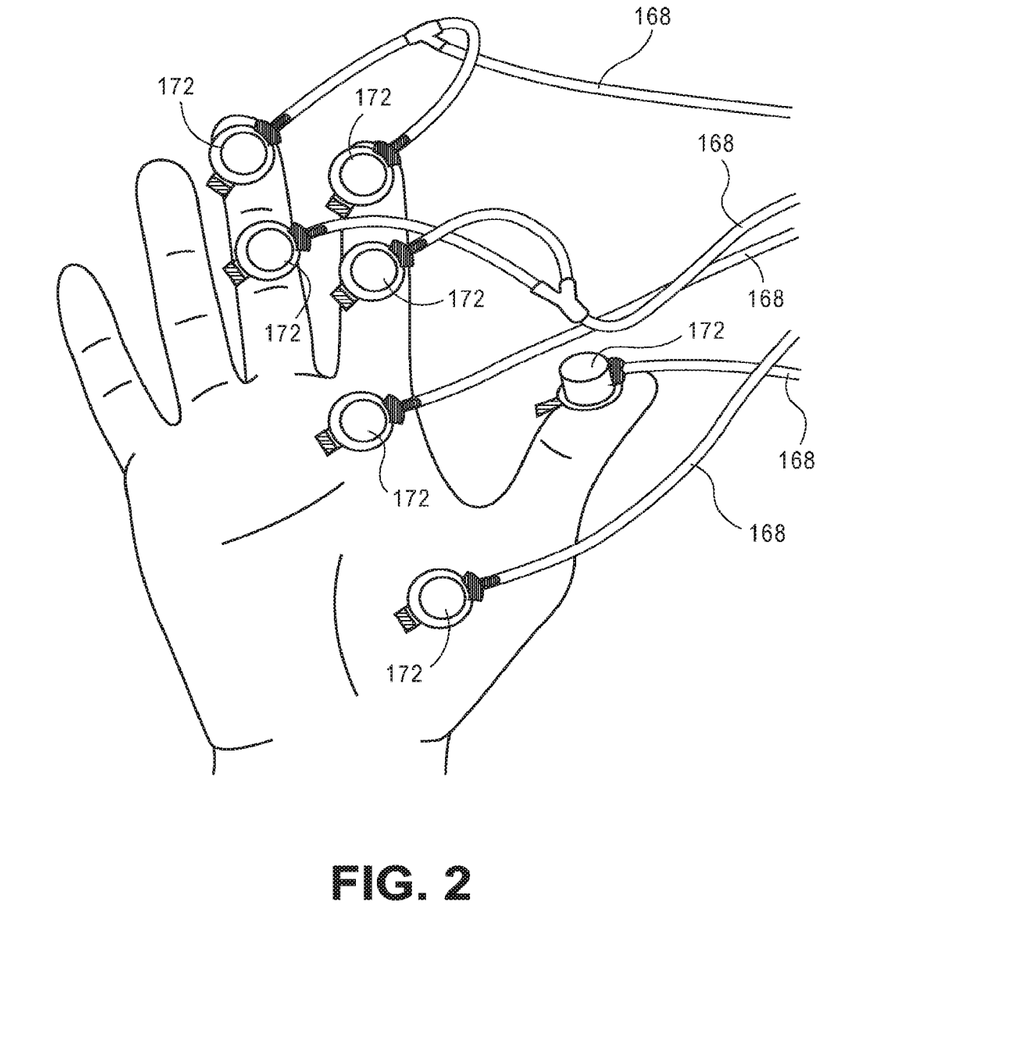
FIG. 2 is a diagrammatic illustration of multiple applicators affixed to a hand in accordance with an example implementation of the present disclosure.
Figure 3:
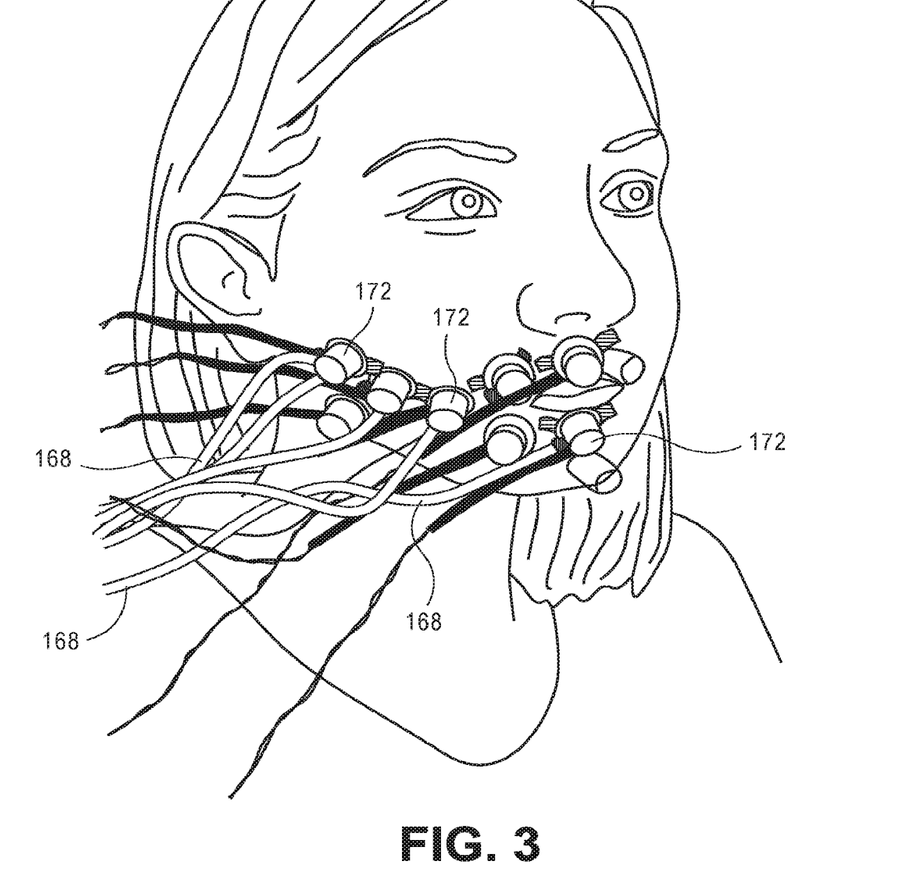
FIG. 3 is a diagrammatic illustration of multiple applicators affixed to a face in accordance with an example implementation of the present disclosure.

FIGS. 2 and 3 are examples of multiple applicators 172 being affixed to the skin of a subject. For example, the applicators 172 can be affixed to a hand of the subject as shown in FIG. 2 or affixed to a face of the subject as shown in FIG. 3. When affixing the applicators 172 to the hand, medical personnel may affix the applicators to the glabrous surface of the skin. When affixed to the skin, the applicators 172 can deliver stimulation pulses to skin according to the stimulation pattern.

FIG. 4 illustrates an example pneumatic switch 160 according to an example implementation of the present disclosure. As shown, the pneumatic switch 160 includes a first pneumatic solenoid valve 402, a second pneumatic solenoid valve 406, and a third pneumatic solenoid valve 410, which are all connected to a manifold 414.

In response to a first selection signal (for example, a first bit of a digital signal), the first pneumatic solenoid valve 402 connects the regulated high pressure to the manifold 414. In response to a second selection signal, the second pneumatic solenoid valve 406 connects the regulated low pressure to the manifold 414. In response to a third selection signal, the third pneumatic solenoid valve 410 connects the atmospheric pressure to the manifold 414.

The outputs of the pneumatic solenoid valves 402, 406, 410 are connected to inputs of a manifold 414. The manifold 414 can establish a connection between the one of the high pressure reservoir 136, the low pressure reservoir 140, and/or atmosphere based on the selection signal. For example, the output of the manifold 414 is connected to the input of the quick-release port 164 to allow the applicator 172 to deliver a pulsed stimulation pulse based on the applicator 172 subjecting the skin to pressurized air, subjecting the skin to vacuum pressure, or subjecting the skin to atmosphere.

FIG. 5 illustrates another example implementation of a tactile stimulation device 500. Many features of the tactile stimulation device 500 may be implemented similarly to those of the tactile stimulation device 100. The tactile stimulation device 500 includes an enclosure 504. The enclosure 504 includes an atmospheric port 508 to provide a fluid connection between atmosphere and the inside of the enclosure 504, or directly to the pneumatic switch 160. The atmospheric port 508 may be a simple opening, but may be designed to decrease noise escaping from the enclosure 504. The atmospheric port 508 may be used when the enclosure 504 is airtight enough that an inside of the enclosure 504 does not remain at atmospheric pressure when vacuum or high pressure is introduced to the inside of the enclosure 504.

Power/charging circuitry 512 receives power from the charging port 108 and can distribute power to the various powered components of the tactile stimulation device 500 even while the battery 112 is being charged. The tactile stimulation device 500 includes a dual-mode compressor 516 that is connected to the high pressure reservoir 136 and the low pressure reservoir 140. During a first mode of operation, the dual-mode compressor 516 supplies pressurized air to the high pressure reservoir 136. During a second mode operation, the dual-mode compressor 516 generates a vacuum pressure to remove air from the low pressure reservoir 140. The controller 120 controls operation of the dual-mode compressor 516. The dual-mode compressor 516 may operate from power provided by the power/charging circuitry 512 or from an independent source of power.

Figure 6:
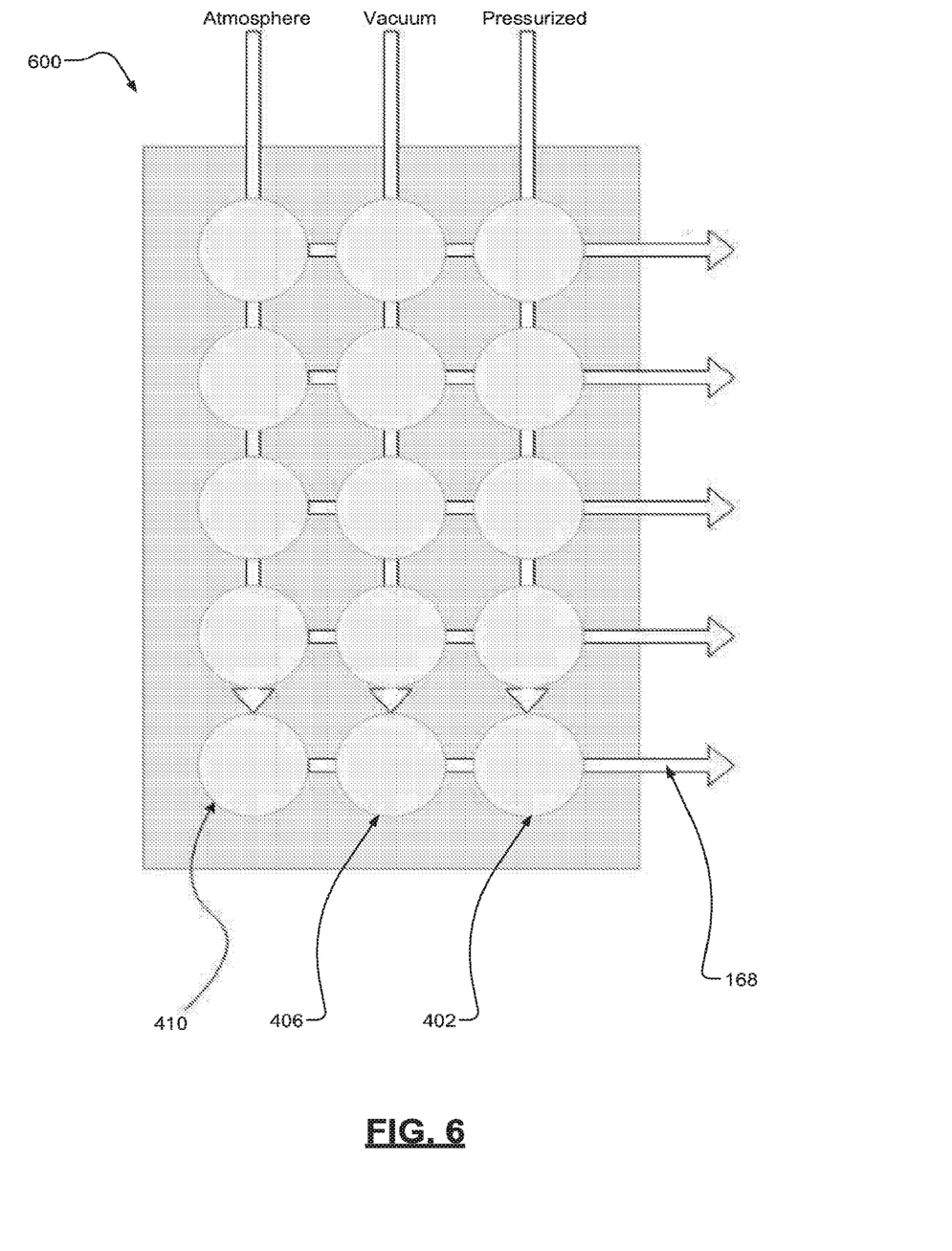
FIG. 6 is a schematic illustration of a pneumatic switch of the tactile stimulation device in accordance with another example implementation of the present disclosure.

FIG. 6 is a schematic of an example implementation of a 5-gang pneumatic switch 600. As shown, the pneumatic switch 600 includes multiple pneumatic solenoids 402 connected to the output of the high pressure regulator 128. The pneumatic switch 600 also includes multiple pneumatic solenoids 406 connected to the output of the low pressure regulator 132 and multiple pneumatic solenoids 410 connected to atmosphere. By controlling the pneumatic solenoids 402, 406, and 410, one of high pressure, low pressure, and vacuum can be individually connected to respective channels (outlet conduits 168). These positively-controlled solenoids prevent cross-talk between the channels.

Figure 7:
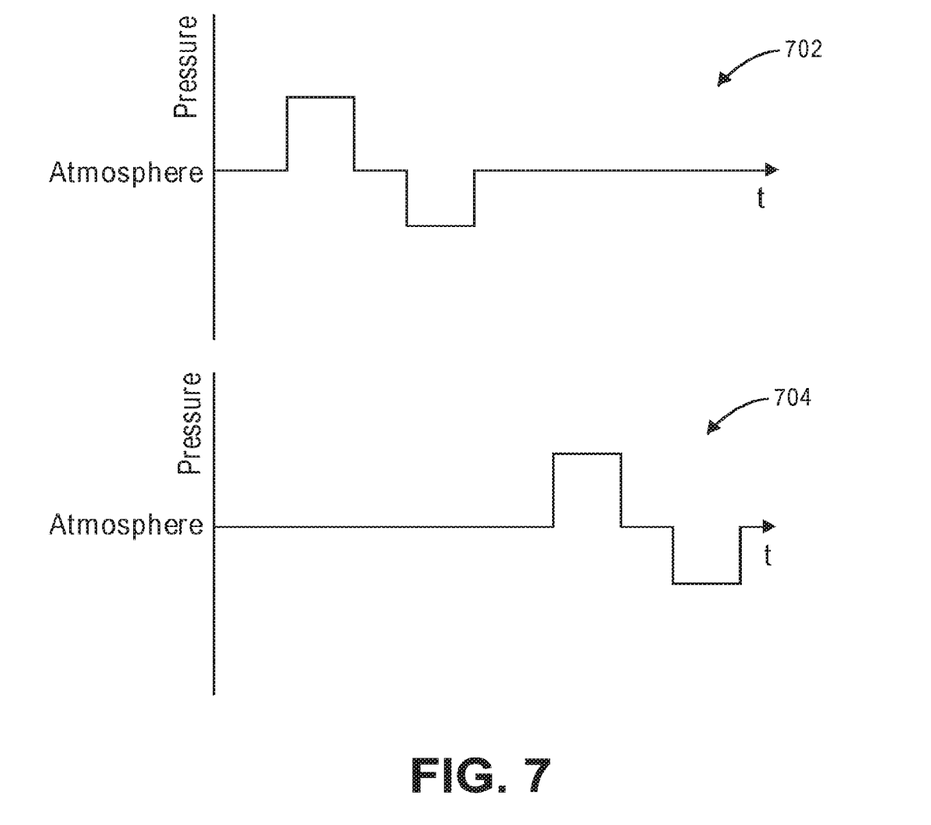
FIG. 7 is a waveform illustrating an example tactile stimulation for first and second applicators of the tactile stimulation device according to an example implementation of the present disclosure.

FIG. 7 includes example waveforms 702, 704 illustrating biphasic pressures (e.g., pressurized fluid) provided to a first applicator 172 and a second applicator 174, respectively, according to a stimulation pattern. In an example implementation, the tactile stimulation device 100 is capable of generating biphasic pneumatic pulses with sub-20 millisecond rise/fall times. In waveform 702, the pressure begins at atmospheric. Then, by opening the pneumatic solenoid 402, a pulse of pressurized fluid is delivered to the first applicator 172 for a first predetermined time period. After the first predetermined time period, the pneumatic solenoid 402 is closed and the pneumatic solenoid 410 is opened to connect the first applicator 172 to atmosphere for a second predetermined time period. After the second predetermined time period, the pneumatic solenoid 410 is closed and the pneumatic solenoid 406 is opened to connect the first applicator 172 to the vacuum pressure for a third predetermined time period. Finally, the pneumatic solenoid 406 is closed and the pneumatic solenoid 410 is opened to connect the first applicator 172 to atmosphere.

The pulse length may be measured from the beginning of the high pressure phase to the end of the vacuum phase. As an example, the pulse length may be 40 milliseconds or 80 milliseconds. Returning the pressure to atmospheric between the high pressure and vacuum phases of the pulse reduces the amount of vacuum expended compared to directly transitioning from high pressure to vacuum. The rise time and fall time may be on the order of 10 milliseconds with outlet conduits 168 having a length on the order of 2 meters. The displacement of the skin by the pulse may be 2 millimeters.

Waveform 704 may be constructed identically to waveform 702, but with solenoids corresponding to the second channel instead of the first channel. While FIG. 7 shows the pulses in waveforms 702 and 704 completely non-overlapping, the pulses may at least partially overlap in various implementations.

CONCLUSION

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A tactile stimulation device comprising:
at least one pneumatic switch, wherein the at least one pneumatic switch includes a plurality of solenoids, wherein a first solenoid of the plurality of solenoids is associated with a high pressure, wherein a second solenoid of the plurality of solenoids is associated with a vacuum pressure, wherein a third solenoid of the plurality of solenoids is associated with an atmospheric pressure, wherein the high pressure is greater than the atmospheric pressure, wherein the atmospheric pressure is greater than the vacuum pressure;
an applicator connected to the at least one pneumatic switch, wherein the at least one pneumatic switch is configured to connect the applicator to the plurality of solenoids; and
a controller operatively connected to the at least one pneumatic switch,
wherein the controller is configured to generate one or more selection signals configured to cause the at least one pneumatic switch to adjust a connection of the applicator to at least one of the first solenoid associated with the high pressure, the second solenoid associated with the vacuum pressure, or the third solenoid associated with the atmospheric pressure to stimulate a nerve ending of a user,
wherein the at least one pneumatic switch is configured to switch between a resting state and one or more simulated states
when the at least one pneumatic switch is in the resting state, the third solenoid is configured to supply the atmospheric pressure to the applicator.

2. The tactile stimulation device as recited in claim 1, wherein the controller is further configured to control the connection of the at least one pneumatic switch to connect the applicator to at least one of the first solenoid associated with the high pressure, the second solenoid associated with the vacuum pressure, or the third solenoid associated with the atmospheric pressure according to a predetermined stimulation pattern.

3. The tactile stimulation device as recited in claim 2, further comprising an input device connected to the controller.

4. The tactile stimulation device as recited in claim 3, wherein the input device is configured to provide data representing the predetermined stimulation pattern to the controller.

5. The tactile stimulation device as recited in claim 1, further comprising:
an enclosure including a quick-release port configured to connect the applicator to the at least one pneumatic switch;
a high pressure reservoir disposed in the enclosure;
a low pressure reservoir disposed in the enclosure; and
a compressor connected to the high pressure reservoir and the low pressure reservoir.

6. The tactile stimulation device as recited in claim 5, wherein the compressor comprises a dual-mode compressor that is configured to supply pressurized air to the high pressure reservoir during a first mode of operation and is configured to generate the vacuum pressure to remove air from the low pressure reservoir during a second mode of operation.

7. The tactile stimulation device as recited in claim 6, further comprising power/charging circuitry configured to supply power to the controller and the dual-mode compressor.

8. The tactile stimulation device as recited in claim 5, wherein the plurality of pneumatic solenoids are connected to the high pressure reservoir.

9. The tactile stimulation device as recited in claim 5, wherein the plurality of pneumatic solenoids are connected to the low pressure reservoir.

10. The tactile simulation device as recited in claim 1, wherein when the at least one pneumatic switch is in a first simulated state of the one or more simulated states, the first solenoid is configured to supply the high pressure to the applicator, wherein when the at least one pneumatic switch is in a second simulated state of the one or more simulated states, the second solenoid is configured to supply the vacuum pressure to the applicator.

11. The tactile simulation device as recited in claim 10, wherein the at least one pneumatic switch is configured to switch to the resting state between the first simulated state and the second simulated state.

12. A tactile stimulation device comprising:
an enclosure;
a high pressure reservoir disposed in the enclosure;
a low pressure reservoir disposed in the enclosure;
a compressor connected to the high pressure reservoir and the low pressure reservoir;
at least one pneumatic switch disposed within the enclosure and connected to the high pressure reservoir and the low pressure reservoir, wherein the at least one pneumatic switch includes a plurality of solenoids, wherein a first solenoid of the plurality of solenoids is associated with a high pressure, wherein a second solenoid of the plurality of solenoids is associated with a vacuum pressure, wherein a third solenoid of the plurality of solenoids is associated with an atmospheric pressure, wherein the high pressure is greater than the atmospheric pressure, wherein the atmospheric pressure is greater than the vacuum pressure;
an applicator connected to the at least one pneumatic switch, wherein the at least pneumatic switch is configured to connect the applicator to the plurality of solenoids; and
a controller disposed within the enclosure and operatively connected to the at least one pneumatic switch,
wherein the controller is configured to generate one or more selection signals configured to cause the at least one pneumatic switch to adjust a connection of the applicator to at least one of the first solenoid associated with the high pressure, the second solenoid associated with the vacuum pressure, or the third solenoid associated with the atmospheric pressure to stimulate a nerve ending of a user,
wherein the at least one pneumatic switch is configured to switch between a resting state and one or more simulated states,
when the at least one pneumatic switch is in the resting state, the third solenoid is configured to supply the atmospheric pressure to the applicator.

13. The tactile stimulation device as recited in claim 12, wherein the controller is further configured to control the connection of the at least one pneumatic switch according to a predetermined stimulation pattern.

14. The tactile stimulation device as recited in claim 13, further comprising an input device connected to the controller.

15. The tactile stimulation device as recited in claim 14, wherein the input device is configured to provide data representing the predetermined stimulation pattern to the controller.

16. The tactile stimulation device as recited in claim 12, wherein the compressor comprises a dual-mode compressor that is configured to supply pressurized air to the high pressure reservoir during a first mode of operation and is configured to generate the vacuum pressure to remove air from the low pressure reservoir during a second mode of operation.

17. The tactile stimulation device as recited in claim 16, further comprising power/charging circuitry disposed within the enclosure and configured to supply power to the controller and the dual-mode compressor.

18. The tactile stimulation device as recited in claim 12, wherein the plurality of pneumatic solenoids are connected to the high pressure reservoir.

19. The tactile stimulation device as recited in claim 12, wherein the plurality of pneumatic solenoids are connected to the low pressure reservoir.

20. A tactile stimulation device comprising:
an enclosure;
a high pressure reservoir disposed in the enclosure;
a low pressure reservoir disposed in the enclosure;
a dual-mode compressor disposed in the enclosure and connected to the high pressure reservoir and the low pressure reservoir, the dual-mode compressor configured to supply pressurized air to the high pressure reservoir during a first mode of operation and is configured to generate vacuum pressure to remove air from the low pressure reservoir during a second mode of operation;
at least one pneumatic switch disposed in the enclosure and connected to the high pressure reservoir and the low pressure reservoir, wherein the at least one pneumatic switch includes a plurality of solenoids, wherein a first solenoid of the plurality of solenoids is associated with a high pressure, wherein a second solenoid of the plurality of solenoids is associated with a vacuum pressure, wherein a third solenoid of the plurality of solenoids is associated with an atmospheric pressure, wherein the high pressure is greater than the atmospheric pressure, wherein the atmospheric pressure is greater than the vacuum pressure;

an applicator connected to the at least one pneumatic switch, wherein the at least pneumatic switch is configured to connect the applicator to the plurality of solenoids;

a controller disposed in the enclosure and operatively connected to the at least one pneumatic switch; and a battery disposed in the enclosure and configured to provide power to the controller and the dual-mode compressor, wherein the controller is configured to generate one or more selection signals configured to cause the at least one pneumatic switch to adjust a connection of the applicator to at least one of the first solenoid associated with the high pressure, the second solenoid associated with the vacuum pressure, or the third solenoid associated with the atmospheric pressure to stimulate a nerve ending of a user, wherein the at least one pneumatic switch is configured to switch between a resting state and one or more simulated states, when the at least one pneumatic switch is in the resting state, the third solenoid is configured to supply the atmospheric pressure to the applicator.

\* \* \* \* \*